United States Patent [19]

Hanotier

[11] 3,996,111
[45] Dec. 7, 1976

[54] RECOVERING ETHYLPHENOL FROM DECOMPOSITION PRODUCTS OF DIETHYLBENZENE MONOHYDROPEROXIDE

[75] Inventor: Jacques Daniel Victor Hanotier, Lambert, Belgium

[73] Assignee: Labofina S.A., Brussels, Belgium

[22] Filed: Oct. 28, 1975

[21] Appl. No.: 626,264

[52] U.S. Cl. .................................. 203/37; 203/73; 260/618 A; 260/624 A
[51] Int. Cl.$^2$ ...................... B01D 3/00; B01D 3/34; C07C 29/00
[58] Field of Search .................. 203/36, 37, 73; 260/618 A, 618 C, 624 A

[56] References Cited
UNITED STATES PATENTS

| | | | |
|---|---|---|---|
| 2,727,074 | 12/1955 | Bewley | 203/36 |
| 2,824,048 | 2/1958 | Hupe et al. | 203/37 |
| 2,992,169 | 7/1961 | Gregory et al. | 203/36 |
| 3,168,577 | 2/1965 | Weinstein et al. | 260/624 A |
| 3,592,857 | 7/1971 | Shinohara | 260/618 C |

*Primary Examiner*—Jack Sofer

[57] ABSTRACT

A process for recovering and separating substantially pure ethylphenol and substantially pure diethylbenzene from a mixture resulting from the decomposition of diethylbenzene monohydroperoxide and consisting essentially of diethylbenzene, ethylphenol and oxygenated by-products thereof, said process comprising distilling said mixture in a first distillation step operated under reduced pressure to separate a distillate comprising essentially diethylbenzene from a first residue comprising ethylphenol and the oxygenated by-products of said mixture, withdrawing said residue and distilling said first residue in a second distillation step operated under reduced pressure to separate a distillate consisting essentially of ethylphenol from a second residue containing from 30 to 40 mole % of ethylphenol in admixture with said oxygenated by-products, withdrawing said second residue and mixing it with the distillate from the first distillation step, treating the resulting mixture with an aqueous alkaline solution to form an aqueous extract and a raffinate, recovering ethylphenol from said extract and distilling said raffinate in a third distillation step to obtain a distillate consisting essentially of diethylbenzene and a residue consisting essentially of ethyl-acetophenone and 1-(ethylphenyl) ethanol, said extract is neutralized with a mineral acid to regenerate ethylphenol as a separate organic phase which is then mixed with the residue from said first distillation column, for purification in said second distillation column.

3 Claims, 1 Drawing Figure

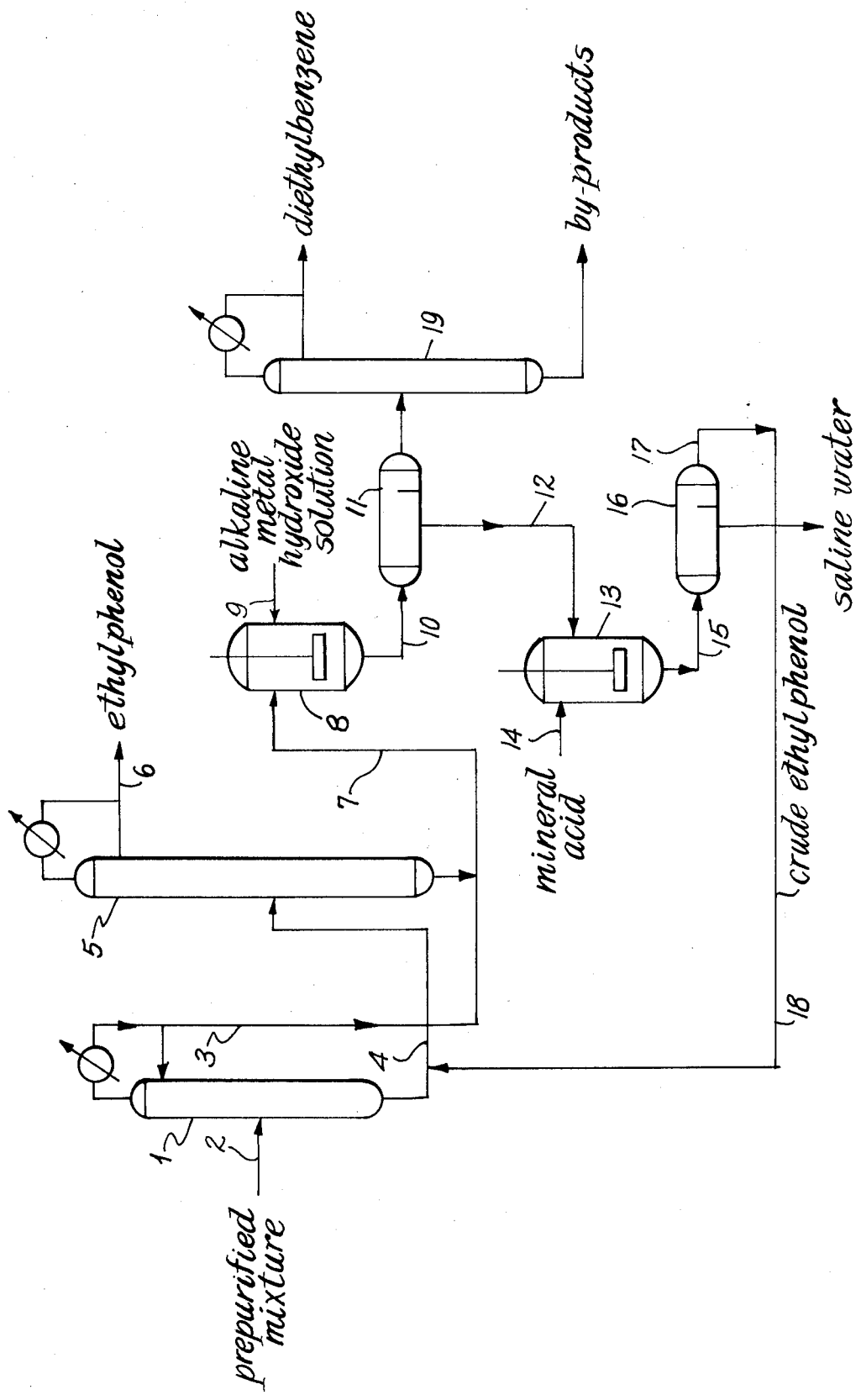

3,996,111

RECOVERING ETHYLPHENOL FROM DECOMPOSITION PRODUCTS OF DIETHYLBENZENE MONOHYDROPEROXIDE

BACKGROUND OF THE INVENTION

This invention relates to a process for producing ethylphenol and acetaldehyde from diethylbenzene. It relates more particularly to a process for separating pure ethylphenol and recovering pure unreacted diethylbenzene from the products resulting from the decomposition of the diethylbenzene mono-hydroperoxide produced in the first step of the process.

Diethylbenzene is converted into ethylphenol and acetaldehyde by a process having two primary steps. These steps are the autoxidation of diethylbenzene to diethylbenzene monohydroperoxide and the decomposition of the diethylbenzene monohydroperoxide into ethylphenol and acetaldehyde. Such a process is described in U.S. patent application Ser. No. 334,084, now U.S. Pat. No. 3,923,909, filed on Feb. 20, 1974. The reactions involved in the process are as follows:

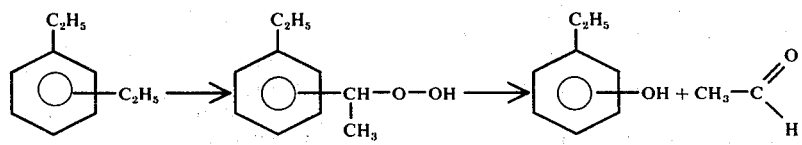

The diethylbenzene feed may be any isomeric mixture or any pure isomer, i.e., m-diethylbenzene which is converted to m-ethylphenol.

The decomposition of the monohydroperoxide produced in the first step proceeds easily in the presence of a strong acid which does not interfere with the reaction and in the presence of a solvent. Such solvent usually is a low molecular weight aliphatic alcohol or ketone. Preferably, this decomposition reaction is carried out in the presence of sulfuric acid and an anhydrous ketone.

The selectivity of the above process with respect to the production of diethylbenzene monohydroperoxide depends on different factors, more particularly, on the degree of conversion, which preferably ranges between 5 and 30%. It therefore is necessary that unreacted diethylbenzene be recovered as completely as possible for recycle. However, this diethylbenzene must be recovered in a high degree of purity and particularly, must be free from any phenolic compound which would inhibit oxidation. It also is necessary that the ethylphenol product which is used for producing pharmaceutical products, stabilizers and other valuable derivatives, be recovered as pure as possible.

The decomposition mixture containing ethylphenol and unreacted diethylbenzene is a rather complex system. In addition, to light components (acetaldehyde, ketone, water) which are easily removed, the mixture contains other components which may be roughly divided into three groups: (1), unreacted diethylbenzene, ethylphenol and oxygenated by-products, i.e. ethylacetophenone and 1-(ethylphenyl)ethanol; (2), heavier by-products such as diacetylbenzene, 1-(acetylphenyl)ethanol, resorcinol, etc. and (3), non-volatile compounds consisting of salts and tarry materials. By using known methods, such as vacuum evaporation, steam distillation and fractional distillation, the compounds of the first group are easily separated from the others. It is then necessary to recover substantially pure ethylphenol and diethylbenzene from the mixture containing such compounds together with the oxygenated by-products. Diethylbenzene, which is more volatile than the other components of the mixture, can easily be separated by distillaton. However, further resolution of the mixture by distillation is impossible because of the formation of an azeotrope between ethylphenol and the oxygenated by-products.

Methods are known which can be used to separate ethylphenol from the by-products. For instance, since ethylphenol is an acidic compound, it can be extracted by a strong base, e.g. by an aqueous solution of NaOH or KOH. Generally, phase separation does not take place upon such treatment, unless an appropriate solvent, which may be diethylbenzene, is used. Ethylphenol is then regenerated by treating the aqueous phase by an acid. However, the by-products are not completely eliminated, even after many successive washings, so that a careful distillation is still required to obtain pure ethylphenol. Moreover, another disadvantage is that this process consumes large amounts of base and of acid.

Another method which can be employed comprises carrying out an extractive distillation with a compound such as triethyleneglycol, triethanolamine or any tertiary amine, for example tri-n-octylamine, capable of association with ethylphenol. By so doing, the relative volatility of ethylphenol is sufficiently lowered for the by-products to be removed overhead. However, this extractive distillation is unsatisfactory in that it requires the use of large amounts of extracting agent and of a very efficient distillation column. Also, it is often difficult to avoid loss of some ethylphenol overhead. Moreover, ethylphenol which is withdrawn as bottoms still needs a further distillation to be obtained in the desired purity.

It is now an object of the present invention to provide a simple and efficient process for recovering pure ethylphenol from a mixture containing diethylbenzene, ethylphenol and the oxygenated by-products thereof.

It is an additional object of the present invention to provide a method for recovering pure diethylbenzene and pure ethylphenol from a prepurified mixture resulting from the decomposition of diethylbenzene monohydroperoxide.

SUMMARY OF THE INVENTION

In accordance with the present invention, a process for recovering and separating substantially pure ethylphenol and substantially pure diethylbenzene from a mixture resulting from the decomposition of diethylbenzene monohydroperoxide and consisting essentially of diethylbenzene, ethylphenol and oxygenated by-products thereof, i.e. ethylacetophenone and 1-(ethylphenyl)ethanol is presented, said process comprising distilling said mixture in a first distillation step to separate a distillate comprising predominantly diethylbenzene from a first residue comprising the oxygenated components of said mixture, withdrawing said residue and distilling said residue in a second distillation step to separate a distillate consisting substantially of pure ethylphenol from a second residue containing from 30 to 40 mole % of ethylphenol in admixture with the oxygenated by-products, withdrawing said second residue and mixing it with the distillate from the first distillation step, treating the resulting mixture with an aqueous alkaline solution to form an aqueous extract and a raffinate, recovering ethylphenol from said extract and distilling said raffinate in a third distillation step to obtain a distillate consisting of substantially pure diethylbenzene.

In a preferred embodiment of the present invention, the process comprises the steps of introducing continuously a pre-purified mixture resulting from the decomposition of diethylbenzene monohydroperoxide and consisting essentially of diethylbenzene, ethylphenol and oxygenated by-products thereof into a first distillation column operated under reduced pressure to separate a distillate comprising predominantly at least 99% of the diethylbenzene initially present in said mixture from a first residue consisting of ethylphenol and the oxygenated by-products thereof, withdrawing said first residue from said first distillation column and introducing continuously said first residue in admixture with crude ethylphenol recovered from a further stage into a second distillation column, operated under reduced pressure to separate a distillate consisting of substantially pure ethylphenol from a second residue containing from 30 to 40 mole % of ethylphenol in admixture with the oxygenated by-products, withdrawing said second residue from said second distillation column and mixing said second residue with the distillate from the first distillation column, the resulting mixture being then treated with an aqueous alkaline solution to form an aqueous extract and a raffinate, introducing said raffinate into a third distillation column to separate a distillate consisting of substantially pure diethylbenzene from said raffinate comprising predominantly ethylacetophenone and 1-(ethylphenyl)-ethanol, neutralizing said extract with a mineral acid to regenerate ethylphenol as a separate organic phase which is then mixed with the residue of the first distillation column for purification in the second distillation column.

DESCRIPTION OF THE PREFERRED EMBODIMENTS

A typical mode of practicing the invention will be described with reference to the drawing which is a schematic flow diagram of the process according to the present invention.

As explained above, the reaction mixture resulting from the decomposition of diethylbenzene monohydroperoxide is a fairly complex system. The light components, the heavy by-products and the non-volatile compounds are easily removed, by known methods. The resulting prepurified mixture is substantially composed of unreacted diethylbenzene, ethylphenol, ethylacetophenone and 1-(ethylphenyl)ethanol. The relative proportion of these components in the prepurified mixture depends upon the selectivity of the oxidation reaction by which they were prepared. This mixture may contain from about 30 to 50 mole % of diethylbenzene, 50 to 60 mole % of ethylphenol and 1 to 15 mole % of oxygenated by-products.

The prepurified mixture is introduced into distillation column 1 through line 2. Diethylbenzene boils distinctly lower than the other components of the mixture. Thus, at atmospheric pressure, the boiling point of m-diethylbenzene is 181° C whereas it is 218° C for m-ethylphenol, 232° C for m-ethylacetophenone and 240° C for the corresponding carbinol. Accordingly, diethylbenzene is easily separated overhead, through line 3, from the other components. The latter are withdrawn as bottoms through line 4. In order to avoid any contamination of ethylphenol by diethylbenzene in further operation, this distillation has to be so conducted as to have a residue virtually free from diethylbenzene. By contrast and in accordance with the process of the present invention, some ethylphenol in the distillate may be tolerated since it will be separated from diethylbenzene in a further stage, as hereinafter explained. The fractional distillation in column 1 is conducted in conventional manner, under atmospheric or subatmospheric pressure. For practical reasons, however, it is preferable to operate under reduced pressure, e.g. 40 mm Hg. The other conditions, i.e. column efficiency and reflux ratio can be easily calculated for optimum operation.

The residue from column 1 is mixed in line 4 with crude ethylphenol recovered from a further stage as hereinafter described, and fed into distillation column 5. From the top of column 5, practically pure ethylphenol is recovered via line 6. According to this invention, a requisite condition for recovering pure ethylphenol overhead is to leave as bottoms an azeotropic mixture comprising ethylphenol and the oxygenated by-products, e. g., ethylacetophenone and 1-(ethylphenyl)ethanol. Preferably, the residue from distillation column 5 will contain from at least 30 to about 40 mole % of ethylphenol. The portion of ethylphenol left in the residue depends primarily upon the amount of by-products present therewith in the feed. As a general rule, it will be lower as the selectivity of the oxidation step of the process is higher. To achieve the separation of pure ethylphenol, column 5 must have more than 15 theoretical plates, preferably from about 20 to 25 theoretical plates depending on the reflux ratio, the composition of the feed and the degree of resolution. Preferably, this distillation is conducted under reduced pressure, as in column 2.

The residue from column 5 is mixed in line 7 with the distillate from column 1 and the resulting mixture is charged into extractor 8. This mixture comprises diethylbenzene, oxygenated by-products and ethylphenol. Separation of the latter from the other components is ensured by treating the mixture with an aqueous solution of an alkaline metal hydroxide, admitted from line 9, in at least the stoechiometric amount required for transforming ethylphenol into the corresponding alkaline salt. Generally, this hydroxide is provided in a 10 to 20 weight % solution and, to secure a complete extraction of ethylphenol, it is used in excess, for instance an excess of 10 to 20%, over the stoechiometric amount. It is also desirable in carrying out this treatment that efficient agitation be provided in order to ensure intimate contact between the mixture to be treated and the aqueous solution of hydroxide.

The mixture from vessel 8 is fed through line 10 into settling tank 11 as a two phase mixture. In settling tank 11 the phases are allowed to separate. This operation is facilitated by the presence of diethylbenzene which also acts as an extraction solvent for the by-products to be removed. The aqueous phase is discharged via line 12 into neutralization vessel 13 wherein it is treated under agitation by a mineral acid, e.g., HCl or $H_2SO_4$.

Such acid is admitted as a concentrated aqueous solution from line 14. An alternate procedure is to bubble a gaseous acid such as carbon dioxide into the mixture to be acidified. The acid is used in at least the stoechiometric amount necessary to regenerate ethylphenol which then separates as a distinct layer. The neutralized mixture is transferred through line 15 into settling tank 16 where crude ethylphenol is allowed to separate from saline water. The latter is discharged through line 17 to be discarded as waste after the recovery of minor amounts of ethylphenol dissolved therein. Crude ethylphenol, which contains some oxygenated by-products and minor amounts of diethylbenzene, is withdrawn through line 18 and is mixed with the residue from column 1 as hereinabove described.

The organic phase from settling tank 11 consists mainly of diethylbenzene together with ethylacetophenone and 1-(ethylphenyl)ethanol. The diethylbenzene is to be recovered for recycle to the oxidation stage of the process. This operation is carried out by conventional distillation in column 19. Substantially pure diethylbenzene is recovered overhead while the by-products are taken off as bottoms.

The following example is given by way of further illustration of the process of the present invention. The process carried out in this Example is described in terms of the drawing.

EXAMPLE

A mixture comprising 52.4 mole % of m-ethylphenol, 39.6 mole % of m-diethylbenzene and 10.7 mole % of oxygenated by-products, particularly m-ethylacetophenone and 1-(m-ethylphenyl) ethanol is fed into distillation column 1 which has 12 rectification stages. The column is operated at 40 mm Hg. The reflux ratio is adjusted to a value of 0.75 so as to recover overhead a mixture comprising as much as 99.5% of the diethylbenzene present in the feed and about 5% of the ethylphenol. The actual composition of each effluent of the column is shown in the following Table. It can be seen that the bottoms residue is almost free from diethylbenzene (less than 0.35 mole % of diethylbenzene.

The residue from this first distillation is mixed with crude ethylphenol from further processing as explained herein-above. The resulting mixture consists primarily of ethylphenol (84 mole %) and the above described oxygenated by-products (15 mole %). This mixture is fed into distillation column 8 having 21 theoretical plates. This column is operated under a pressure of 40 mm Hg and with a reflux ratio of 1.78 whereby 99% ethylphenol is produced as overheads while a residue comprising 40 mole % of the same is recovered as bottoms.

This second residue is mixed with crude diethylbenzene obtained as overhead from column 1 and the resulting mixture is fed into extraction vessel 8 where it is treated under vigorous stirring by a 10% aqueous solution of caustic soda. This solution is used in an excess of 10%, over the stoechiometric amount necessary to neutralize the ethylphenol present in the feed. The treated mixture containing the sodium salt of ethylphenol is then discharged into settling tank 11 wherein the aqueous alkaline solution is allowed to separate from an organic phase. The aqueous phase is then transferred into acidification tank 13 wherein ethylphenol is regenerated by addition of concentrated sulfuric acid. Crude ethylphenol is separated in settling tank 16 and recycled to distillation column 5 for purification. The organic layer from decanter 11 is transferred into distillation column 19 having 10 theoretical plates. This column is operated under 40 mm Hg with a reflux ratio of 0.3. 99% diethylbenzene is recovered overhead while the oxygenated by-products are removed as bottoms.

The following Table shows the material balance at the main steps of the process in accordance with the present invention.

TABLE

| OPERATION | Products (moles) | | | |
|---|---|---|---|---|
| | DEB | EP | EA+EC | TOTAL |
| Separation of crude diethylbenzene Column 1 | | | | |
| Feed | 36.9 | 52.4 | 10.7 | 100.0 |
| Distillate | 36.7 | 2.6 | 0.5 | 39.8 |
| Residue | 0.2 | 49.8 | 10.2 | 60.2 |
| Separation of purified ethylphenol (column 5) | | | | |
| Feed (residue from column 1 + extract from vessel 15) | 0.3 | 59.6 | 10.9 | 70.8 |
| Distillate | 0.3 | 52.4 | 0.3 | 53.0 |
| Residue | — | 7.2 | 10.6 | 17.8 |
| Alkaline extraction of ethylphenol (vessel 8) | | | | |
| Feed (distillate from column 1 + residue from column 5) | 36.7 | 9.8 | 11.1 | 57.6 |
| Extract | 0.1 | 9.8 | 0.7 | 10.6 |
| Raffinate | 36.6 | — | 10.4 | 47.0 |
| Separation of purified diethylbenzene (column 19) | | | | |
| Feed (raffinate of vessel 11) | 36.6 | — | 10.4 | 47.0 |
| Distillate | 35.9 | — | 0.3 | 36.2 |
| Residue | 0.7 | — | 10.1 | 10.8 |

What is claimed is:

1. A process for recovering and separating substantially pure ethylphenol and substantially pure diethylbenzene from a mixture resulting from the decomposition of diethylbenzene monohydroperoxide and consisting essentially of diethylbenzene, ethylphenol and oxygenated by-products thereof, said process comprising distilling said mixture in a first distillation step to separate a distillate comprising essentially diethylbenzene from a first residue comprising ethylphenol and the oxygenated by-products of said mixture, withdrawing said residue and distilling said first residue in a second distillation step to separate a distillate consisting essentially of ethylphenol from a second residue containing from 30 to 40 mole % of ethylphenol in admixture with said oxygenated by-products, withdrawing said second residue and mixing it with the distillate from the first distillation step, treating the resulting mixture with an aqueous alkaline solution to form an aqueous extract and a raffinate, recovering ethylphenol from said extract and distilling said raffinate in a third distillation step to obtain a distillate consisting essentially of diethylbenzene.

2. The process of claim 1 wherein the mixture of said second residue and said distillate from said first distillation step is treated with an aqueous solution containing from about 10 to 20% by weight of an alkaline metal hydroxide, said solution being used in an excess of 10 to 20% based on the stoechiometric amount required to neutralize the ethylphenol present in said mixture, with formation of an aqueous extract comprising the alkaline salt of ethylphenol, said aqueous extract being separated from the raffinate and being treated with a mineral acid to regenerate the ethylphenol.

3. The process of claim 1 wherein a prepurified mixture is continuously introduced into said first distillation column which is operated under reduced pressure, to separate a distillate comprising at least 99% of the diethylbenzene initially present in said prepurified mixture from said first residue, said first residue is withdrawn from said first distillation column and introduced continuously into admixture with said extract with said admixture being introduced into a second distillation column which is operated under reduced pressure to separate a distillate consisting of substantially pure ethylphenol from said second residue, said second residue is withdrawn from said second distillation column and mixed with said distillate from said first distillation column, the resulting mixture being then treated with an aqueous alkaline solution to form an aqueous extract and a raffinate, said raffinate is introduced into a third distillation column to separate a distillate consisting of substantially pure diethylbenzene from a residue consisting essentially of ethylacetophenone and 1-(ethylphenyl)ethanol, said extract is neutralized with a mineral acid to regenerate ethylphenol as a separate organic phase which is then mixed with the residue from said first distillation column, for purification in said second distillation column.

* * * * *